United States Patent
Cheng et al.

(10) Patent No.: US 8,871,238 B2
(45) Date of Patent: Oct. 28, 2014

(54) MEDICAL DEVICES AND COATINGS THEREFORE COMPRISING BIODEGRADABLE POLYMERS WITH ENHANCED FUNCTIONALITY

(75) Inventors: Peiwen Cheng, Santa Rosa, CA (US); Mingfei Chen, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1328 days.

(21) Appl. No.: 12/064,105

(22) PCT Filed: Aug. 9, 2006

(86) PCT No.: PCT/US2006/031130
§ 371 (c)(1),
(2), (4) Date: Feb. 19, 2008

(87) PCT Pub. No.: WO2007/024492
PCT Pub. Date: Mar. 1, 2007

(65) Prior Publication Data
US 2008/0233168 A1 Sep. 25, 2008

Related U.S. Application Data

(60) Provisional application No. 60/711,991, filed on Aug. 25, 2005.

(51) Int. Cl.
*A61F 2/02* (2006.01)
*A61F 2/04* (2013.01)
*A61K 31/436* (2006.01)
*A61L 27/34* (2006.01)
*A61K 31/00* (2006.01)
*A61L 27/54* (2006.01)
*A61L 31/10* (2006.01)
*A61L 31/16* (2006.01)

(52) U.S. Cl.
CPC ............ *A61L 27/34* (2013.01); *A61K 31/00* (2013.01); *A61L 27/54* (2013.01); *A61L 31/10* (2013.01); *A61L 31/16* (2013.01); *A61L 2300/416* (2013.01)
USPC .......................... 424/423; 623/1.46; 514/291

(58) Field of Classification Search
None
See application file for complete search history.

(56) References Cited

U.S. PATENT DOCUMENTS

2003/0129215 A1  7/2003  Mollison et al.
2005/0208093 A1*  9/2005  Glauser et al. ............... 424/423

FOREIGN PATENT DOCUMENTS

WO  WO2004/021976  3/2004
WO  WO2005/092406  10/2005

OTHER PUBLICATIONS

Liu et al. in Macromolecules 1999, 32, 6881-6884.*
Ishihara et al., "Molecular Deisgn and Preparation of Bioinspired Phospholipid Polymer as Novel Biomaterials" Polymer Preprints. Japan, Society of Polymer Science, JP, vol. 42, No. 2, 2001, pp. 117-118.
Li et al., "Synthesis and Hemocompatibility Evaluation of Novel Segmented Polyurethanes With Phosphatidylcholine Polar Headgroups" Chemistry of Materials, American Chemical Society, Washington US, vol. 10, No. 6, 1988, pp. 1596-1603.
Berrocol et al., "Improving the Blood Compatibility of Ion-Selective Electrodes by Employing Poly(MPC-CO-BMA), A Copolymer Containing Phosphorylcholine, as a Membrane Coating" Analytical Chemistry, American Chemical Society, Columbus, US, vol. 74, No. 15, Aug. 1, 2002, pp. 3644-3648.
Lewis et al., "Phosphorylcholine Coated Stents" Journal of Long-Term Effects of Medical Implants, vol. 12, No. 4, 2002, pp. 231-250.

* cited by examiner

*Primary Examiner* — Dennis Heyer

(57) ABSTRACT

Biodegradable polymers useful for fabricating implantable medical devices and as coatings for medical devices are provided. The biodegradable polymers are biocompatible and can be tuned to provide optimum bioactive agent elution rates as well as degradation rates. Also provided are methods for making medical devices and medical device coatings using the biodegradable polymers.

13 Claims, 7 Drawing Sheets

Polyesters

Poly(ortho esters)

Polyanhydrides

Polyphosphazenes

MEDICAL DEVICES AND COATINGS THEREFORE COMPRISING BIODEGRADABLE POLYMERS WITH ENHANCED FUNCTIONALITY

FIELD OF THE INVENTION

The present invention relates to medical devices and coatings for medical devices comprised of biodegradable polymers having functional side chains. More specifically, the present invention provides medical grade biodegradable polymers and devices made therefrom wherein the medical grade biodegradable polymers comprise homopolymers and copolymers having polyester backbones with desirable functionalized side chains.

BACKGROUND OF THE INVENTION

Implantable medical devices have become increasingly more common over the last 50 years and have found applications in nearly every branch of medicine. Examples include joint replacements, vascular grafts, heart valves, ocular lenses, pacemakers, vascular stents, urethral stents, and many others. However, regardless of the application, implantable medical devices must be biocompatible, that is, they must be fabricated from materials that will not elicit an adverse biological response such as, but not limited to, inflammation, thrombogensis or necrosis. Thus, early medical devices were generally fabricated from inert materials such as precious metals and ceramics. More recently, stainless steel and other metal alloys have replaces precious metals and polymers are being substituted for ceramics.

Generally, implantable medical devices are intended to serve long term therapeutic applications and are not removed once implanted. In some cases it may be desirable to use implantable medical devices for short term therapies. However, their removal may require highly invasive surgical procedures that place the patient at risk for life threatening complications. Therefore, it would be desirable to have medical devices designed for short term applications that degrade via normal metabolic pathways and are reabsorbed into the surrounding tissues.

One of the first bioresorbable medical devices develop was the synthetic absorbable suture marketed as Dexon in the 1960s by Davis and Geck, Inc. (Danbury, Conn.). Since that time, diverse biodegradable polymer-based products have found acceptance as implantable medical devices and implantable medical device coatings, thereby alleviating the need for secondary invasive procedure(s) to remove implanted medical device(s).

Biodegradable polymers can be either natural or synthetic. In general, synthetic polymers offer greater advantages than natural materials in that they can be tailored to give a wider range of properties and more predictable lot-to-lot uniformity than can materials from natural sources. Synthetic polymers also represent a more reliable source of raw materials, ones free from concerns of immunogenicity.

In general, polymer selection criteria for use as biomaterials is to match the mechanical properties of the polymer(s) and degradation time to the needs of the specific in vivo application. The factors affecting the mechanical performance of biodegradable polymers are those that are well known to the polymer scientist, and include monomer selection, initiator selection, process conditions and the presence of additives. These factors in turn influence the polymer's hydrophilicity, crystallinity, melt and glass-transition temperatures, molecular weight, molecular-weight distribution, end groups, sequence distribution (random versus blocky) and presence of residual monomer or additives. In addition, the polymer scientist working with biodegradable materials must evaluate each of these variables for its effect on biodegradation. Known biodegradable polymers include, among others, polyglycolide (PGA), polylactide (PLA) and poly($\epsilon$-caprolactone) (PCA). However, these polymers are generally hydrophobic and their structures are difficult to modify. Consequently, the polymer's physical characteristics are difficult to modify, or tune, to match specific clinical demands. For example, polymers made from PLA are extremely slow to degrade and thus not suited for all applications. To address this deficiency polymer scientists have developed co-polymers of PLA and PCA. However, biodegradation rates remain significantly limited.

Additionally, recent advances in in situ drug delivery has led to the development of implantable medical devices specifically designed to provide therapeutic compositions to remote anatomical locations. Perhaps one of the most exciting areas of in situ drug delivery is in the field of intervention cardiology. Vascular occlusions leading to ischemic heart disease are frequently treated using percutaneous transluminal coronary angioplasty (PTCA) whereby a dilation catheter is inserted through a femoral artery incision and directed to the site of the vascular occlusion. The catheter is dilated and the expanding catheter tip (the balloon) opens the occluded artery restoring vascular patency. Generally, a vascular stent is deployed at the treatment site to minimize vascular recoil and restenosis. However, in some cases stent deployment leads to damage to the intimal lining of the artery which may result in vascular smooth muscle cell hyperproliferation and restenosis. When restenosis occurs it is necessary to either re-dilate the artery at the treatment site, or, if that is not possible, a surgical coronary artery bypass procedure must be performed.

Recently, it has been determined drug-eluting stents coated with anti-proliferative drugs such as, but not limited to, rapamycin and its analogs and paclitaxel have shown great promises in preventing restenosis. However, there is a need to develop additional and potentially more efficacious drug-eluting stents (DES). One critical factor in DES efficacy is the drug elution rate. Drug-elution is generally a factor of the drug's solubility in the polymer coating applied to the stent.

Presently, bio-stable, that is non-resorbable polymers, are used as drug eluting coatings for metal stents. The polymer scientist has many different options when selecting a suitable bio-stable polymer and recently several of the present inventors have made significant advances in turning polymer coatings useful for drug elution (see co-pending U.S. patent application Ser. No. 11/005,463). However, the number and type of bioresorbable polymers is much more limited. Therefore, in order for new bioresorbable polymeric medical devices to be developed which have the same functional diversity as their biostable polymer counterparts, it is necessary to first develop new and useful bioresorbable polymers that can be tuned to match drug solubility and provide greater control over resorbability rates.

SUMMARY OF THE INVENTION

The present invention addresses the problem of providing versatile, tunable biodegradable polymers suitable for a wide range of biomedical applications, specifically as coatings for medical devices, structural components of medical devices or both. Prior art biodegradable polymers are limited to a few select polymer types that are not easily modified and thus limit the material scientist's options when designing medical devices needing specific, controllable degradation rates, hydrophilicity/hydrophobicity and/or compatibility with other biologically active molecules such as drugs.

Prior art biodegradable polymers suitable for implantable medical devices, such as polyglycolide (PGA), polylactide (PLA), poly(dioxanaone) (PDO), trimethylene carbonate (TMC), poly(ε-caprolactone) (PCA) and co-polymers thereof, are linear, non-branched polyesters lacking functional side chains that can be derivatized. Consequently, these polymers have limited applications and are generally hydrophobic and therefore possess relatively slow biodegradation rates.

The present inventors, in seeking to solve the aforementioned problem with prior art biodegradable polymers, have discovered new methods and thus made new biodegradable compositions that can be tuned to possess a wide range of biodegradation rates and compatibility with diverse bioactive molecules. The present inventors have achieved this result by providing polyester backbones with desirable functionalized side chains such as, but not limited to, vinyl, hydroxyl, carboxylic, amine, thiol and phosphoryl choline functional sites for further modification.

In one embodiment of the present invention, functional groups are introduced to a lactone ring followed by ring opening polymerization reactions to yield homopolymers and copolymers having the desired functionality. The resulting polymers can then be used to make medical devices or coatings for medical devices, including drug-eluting medical devices and drug-eluting medical device coatings, using techniques known to those skilled in the art.

In one embodiment of the present invention, an implantable medical device is provided wherein the implantable medical device has a coating comprising a biocompatible, biodegradable polymer of Formula 1:

Formula 1

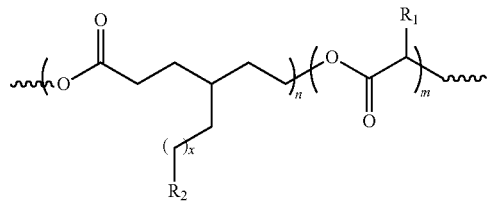

wherein n and m are separately integers from 1 to 100, x is an integer from 0 to 20, $R_1$ is hydrogen or a $C_1$-$C_{10}$ straight chain or branched alkyl or a $C_1$-$C_{10}$ straight chain or branched alkenyl and $R_2$ is a functional group selected from the group consisting of oxo, hydroxyl, carboxylic acid, amino, vinyl, and phosphoryl choline.

In another embodiment of the present invention an implantable medical device is provided wherein the implantable medical device has a coating comprising a biocompatible, biodegradable polymer of Formula 2:

Formula 2

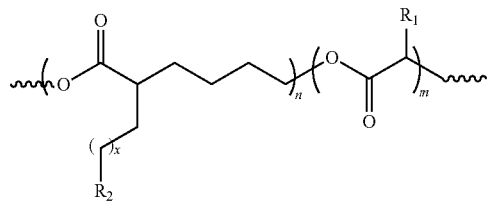

wherein n and m are separately integers from 1 to 100, x is an integer from 0 to 20, $R_1$ is hydrogen or a $C_1$-$C_{10}$ straight chain or branched alkyl or a $C_1$-$C_{10}$ straight chain or branched alkenyl and $R_2$ is a functional group selected from the group consisting of oxo, hydroxyl, carboxylic acid, amino, vinyl, and phosphoryl choline.

In yet another embodiment of the present invention a vascular stent is provided comprising a biodegradable polymer of Formula 3:

Formula 3

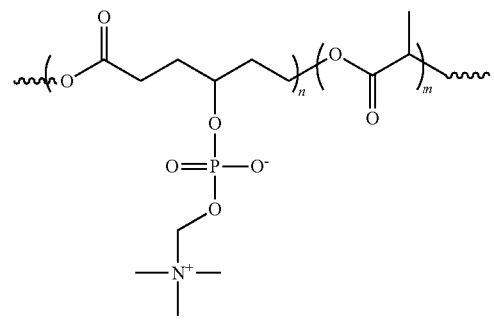

wherein n and m are separately integers from 1 to 100 and wherein the present embodiment may also include at least one bioactive agent, for example zotarolimus (the USAN for a tertrazole-containing rapamycin analogue formally referred to as ABT-578 as described in U.S. Pat. No. 6,015,815).

In still another embodiment of the present invention a vascular stent is provided comprising a biodegradable polymer of Formula 4:

Formula 4

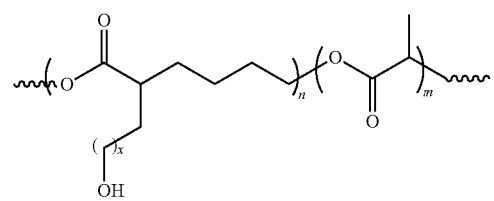

wherein n and m are separately integers from 1 to 100, X is an integer from 0 to 20 and wherein the present embodiment may also include at least one bioactive agent, for example zotarolimus.

DEFINITION OF TERMS USED

Figure 1:
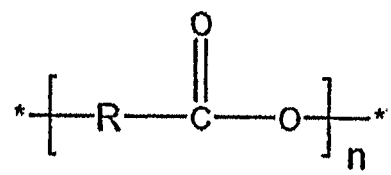
FIG. 1 depicts the chemical structures of the most common biodegradable polymers.
Figure 1:
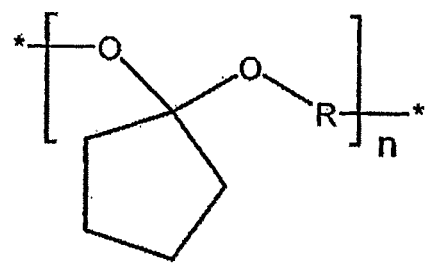
Figure 1:
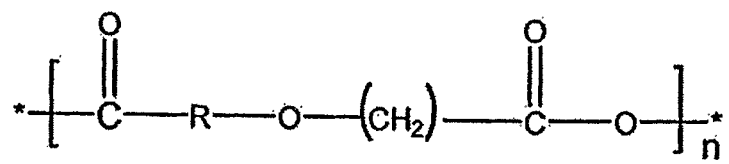
Figure 1:
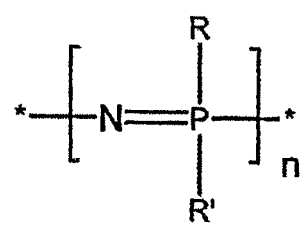

Before proceeding it may be useful to define many of the terms used to describe the present invention. Words and terms of art used herein should be first defined as provided for in this specification, and then as needed as one skilled in the art would ordinarily define the terms.

Animal: As used herein "animal" shall include mammals, fish, reptiles and birds. Mammals include, but are not limited to, primates, including humans, dogs, cats, goats, sheep, rabbits, pigs, horses and cows.

Backbone: As used here in "backbone" refers to the main chain of a polymer or copolymer of the present invention. A "polyester backbone" as used herein refers to the main chain of a biodegradable polymer derived from a lactone ring. See for examples Formulas 1 and 2.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Bioactive agent: As used herein "bioactive agent" shall included anti-proliferative compounds, cytostatic compounds, toxic compounds, anti-inflammatory compounds, chemotherapeutic agents, analgesics, antibiotics, protease inhibitors, statins, nucleic acids, polypeptides, and delivery vectors including recombinant micro-organisms, liposomes, the like (see Drugs below).

Biodegradable: As used herein "biodegradable" refers to a polymeric composition that is biocompatible and subject to being broken down in vitro through the action of normal biochemical pathways. From time-to-time bioresorbable and biodegradable may be used interchangeably, however they are not coextensive. Biodegradable polymers may or may not be reabsorbed into surrounding tissues, however all bioresorbable polymers are considered biodegradable. The biodegradable polymers of the present invention are capable of being cleaved into biocompatible byproducts through chemical- or enzyme-catalyzed hydrolysis.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Compatible: As used herein "compatible" refers to a composition possing the optimum, or near optimum combination of physical, chemical, biological and drug release kinetic properties suitable for a controlled-release coating made in accordance with the teachings of the present invention. Physical characteristics include durability and elasticity/ductility, chemical characteristics include solubility and/or miscibility and biological characteristics include biocompatibility. The drug release kinetic should be either near zero-order or a combination of first and zero-order kinetics.

Delayed Release: As used herein "delayed release" refers to the release of bioactive agent(s) after a period of time and/or after an event or series of events.

Drug(s): As used herein "drug" shall include any bioactive agent having a therapeutic effect in an animal. Exemplary, non limiting examples include anti-proliferatives including, but not limited to, macrolide antibiotics including FKBP 12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-sense nucleotides and transforming nucleic acids.

Functional Side Chain: As used herein "functional side chain" encompasses a first chemical constituent(s) typically capable of binding to a second chemical constituent(s), wherein the first chemical constituent modifies a chemical or physical characteristic of the second chemical constituent. Functional groups associated with the functional side chains include vinyl groups, hydroxyl groups, oxo groups, carboxyl groups, thiol groups, amino groups, phosphor groups and others known to those skilled in the art and as depicted in the present specification and claims.

Hydrophilic: As used herein in reference to the bioactive agent, the term "hydrophilic" refers to a bioactive agent that has a solubility in water of more than 200 micrograms per milliliter.

Hydrophobic: As used herein in reference to the bioactive agent the term "hydrophobic" refers to a bioactive agent that has a solubility in water of no more than 200 micrograms per milliliter.

Lactone: As used herein "lactone" or "lactone ring" refers to a cyclic ester. It is the condensation product of an alcohol group and a carboxylic acid group in the same molecule. Prefixes may indicate the ring size: beta-lactone (4-membered), gamma-lactone (5-membered), delta-lactone (6-membered ring).

DETAILED DESCRIPTION OF THE INVENTION

Biodegradable polymers, either synthetic or natural, are capable of being cleaved into biocompatible byproducts through chemical- or enzyme-catalyzed hydrolysis. This biodegradable property makes it possible to implant them into the body without the need of subsequent surgical removal. Moreover, drugs formulated with these polymers can be released in a controlled manner, by which the drug concentration in the target site is maintained within the therapeutic window. The release rates of the drugs from the biodegradable polymer can be controlled by a number of factors, such as biodegradation rate, physiochemical properties of the polymers and drugs, thermodynamic compatibility between the polymer and drug and the shape of the medical device.

However, most biocompatible polymers are fairly hydrophobic and are not easily derivatized due to a lack of functional side chains. The most frequently encountered biocompatible polymers are polyesters, polyorthoesters, polyanhydrides and polyphosphazes (see FIG. 1). The present invention provides biodegradable polymers having polyester backbones synthesized using ring opening reactions (ROP) where the cyclic precursors have been derivatized such that the resulting monomer subunits have functional side chains.

The biodegradable polymers used to form the coatings and implantable medical devices of the present invention can generally be described as follows:

In one embodiment of the present invention the biocompatible, biodegradable polymers are represented by Formula 1:

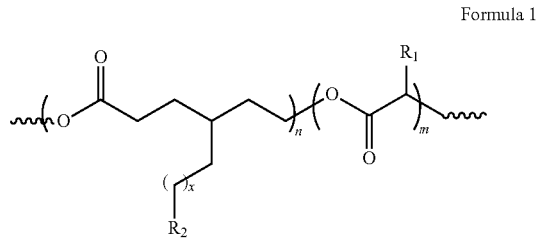

Formula 1 wherein n and m are separately integers from 1 to 100, x is an integer from 0 to 20, $R_1$ is hydrogen or a $C_1$-$C_{10}$ straight chain or branched alkyl or a $C_1$-$C_{10}$ straight chain or branched alkenyl and $R_2$ is a functional group selected from the group consisting of oxo, hydroxyl, carboxylic acid, amino, vinyl, poly(ethylene glycol) (PEG) and phosphoryl choline.

In another embodiment of the present invention the biocompatible, biodegradable polymers are represented by Formula 2:

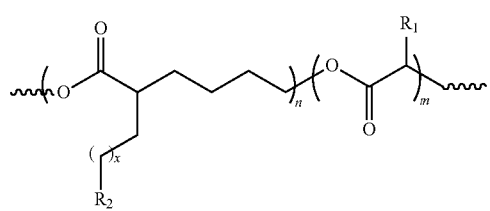

Formula 2 wherein n and m are separately integers from 1 to 100, x is an integer from 0 to 20, $R_1$ is hydrogen or a $C_1$-$C_{10}$ straight chain or branched alkyl or a $C_1$-$C_{10}$ straight chain or branched alkenyl and $R_2$ is a functional group selected from the group consisting of oxo, hydroxyl, carboxylic acid, amino, vinyl, PEG and phosphoryl choline.

In yet another embodiment of the present invention a vascular stent is provided comprising a biodegradable polymer of Formula 3:

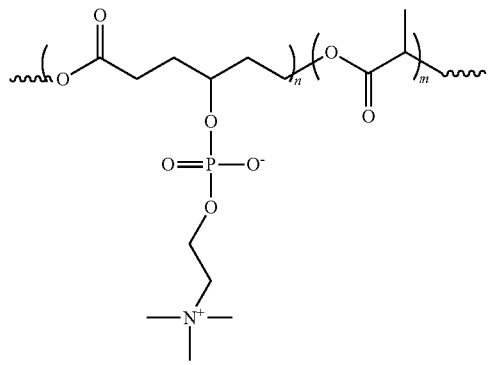

Formula 3 wherein n and m are separately integers from 1 to 100 and wherein the present embodiment may also include at least one bioactive agent, for example zotarolimus (the USAN for a tertrazole-containing rapamycin analogue formally referred to as ABT-578 as described in U.S. Pat. No. 6,015,815).

In still another embodiment of the present invention a vascular stent is provided comprising a biodegradable polymer of Formula 4:

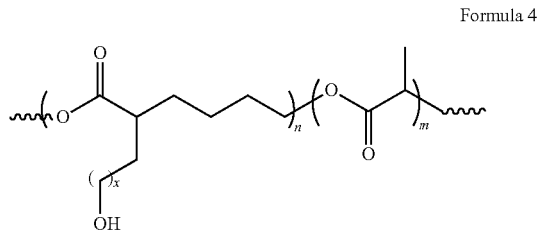

Formula 4 wherein n and m are separately integers from 1 to 100, X is an integer from 0 to 20 and wherein the present embodiment may also include at least one bioactive agent, for example zotarolimus.

In one embodiment of the present invention a hydroxy-functionalized polyester is provided by first subjecting 1,4-cyclohexadione to a Baeyer-Villiger oxidation reaction (or its equivalent) using a per acid such as but not limited to meta-chloroperbenzoic acid (m-CPBA) (alternatively another suitable per acid or Lewis acid in combination with a peroxide can be used in accordance with the teachings of the present invention and as known to those skilled in the art). The resultant reaction product, oxepane-2,5-dione, is then reacted with D,L-lactide using a stannous-2-ethyl-hexanoate ($Sn(Oct)_2$) catalyst. The resulting ring opening (ROP) reaction yields a co-polymer having oxo functionality on the polyester backbone. Next the oxo group is converted to a hydroxyl group using techniques well known to those having ordinary skill in the art of synthetic organic chemistry. For example, it is well known that ketones can be reduced to secondary alcohols through nucleophilic addition (reduction) of the oxo group using hydride reagents such as, but not limited to $LiAlH_4$ and $NaBH_4$. It is understood that where more than one oxo is present and less than the total number of oxo groups are to be reduced that some oxo groups need to be protected. Persons having ordinary skill in the art of synthetic organic chemistry can design suitable protection techniques without undue experimentation.

Once hydroxyl functionality is present on the polyester backbone, myriad other reactions can be performed to modify the polyester backbone at the functionalized site. For example, and not intended as a limitation, the hydroxyl group can be further modified using reductive amination to form an amine functional group, another non-limiting example includes adding phosphoryl choline functionality to the backbone.

Phosphoryl choline functionality is a particularly interesting embodiment of the present invention. Implantable medical devices are generally in intimate contact with surrounding tissues. Thus it is essential that the polymer used (or other material as the case may be) be highly biocompatible. Prior art biodegradable polymers are generally hydrophobic and thus are less biocompatible than the hydrophilic non-bioresorbable counterparts. However, the present inventors have discovered a method for proving hydrophilic functionality to a polyester backbone including a method for providing hydrophilic backbones with phosphoryl choline functionality.

Figure 2:
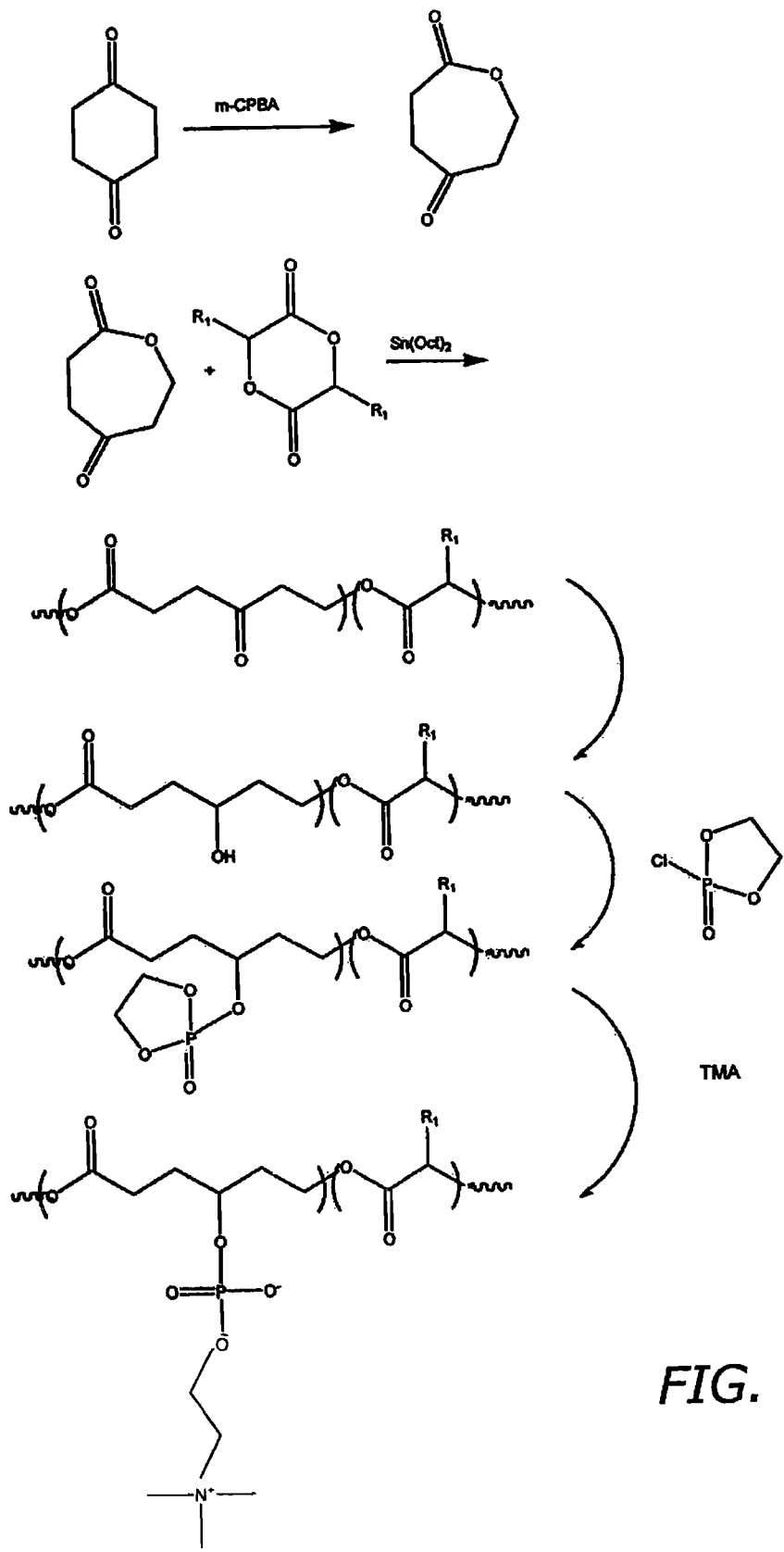
FIG. 2 schematically depicts a non-limiting synthetic method for providing a biocompatible, biodegradable polymer with phosphoryl choline (PC) functionality using a ring opening (ROP) reaction in accordance with the teachings of the present invention.

Phosphoryl choline is a major constituent (phospholipid) of animal cell membranes. Thus, polymers having phosphoryl choline (PC) side chains will demonstrate significantly improved biocompatibility than polymers lacking hydrophilic PC side chains. Moreover, many drugs are passively transported across cell membranes by interacting with the cell's lipid bilayer. Thus PC functionality added to a drug-eluting, or controlled-release, polymeric implantable medical device (or coatings) with a hydrophobic polyester backbone will enhance drug delivery, especially of hydrophobic drugs. FIG. 2 schematically depicts a non-limiting synthetic method for providing a biocompatible, biodegradable polymer with PC functionality using a ROP reaction in accordance with the teachings of the present invention.

Figure 3:
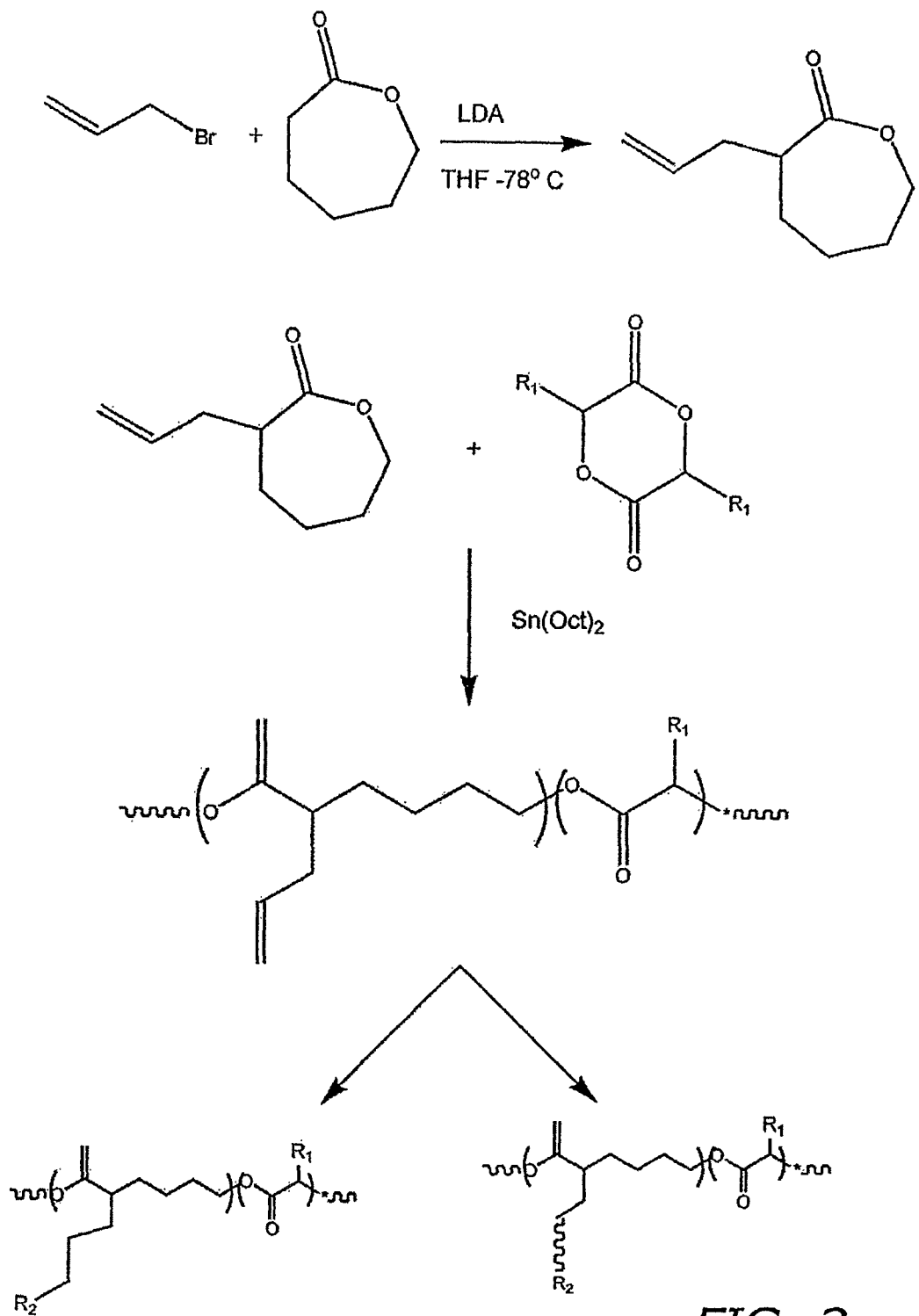
FIG. 3 provides a schematic representation of a non-limiting example of the present invention.

In another embodiment of the present invention, vinyl functionality is provided to biodegradable polymer's polyester backbone. In one embodiment of this example vinyl functionality is added to the alpha carbon of a lactone ring as follows: 3-bromopropene is reacted with ε-caprolactone in the presence of lithium diisopropylamide (LDA) in tetrahydrofuran (−78° C.) to form 3-Allyl-oxepan-2-one. Next the 3-Allyl-oxepan-2-one is added to a solution of D,L-lactide and a ROP reaction is performed using a suitable catalyst such as $Sn(Oct)_2$. The resulting ring opening reaction yields a co-polymer having acrylic functionality on the polyester backbone which serves as a site for further modification as those skilled in the art will readily appreciate. FIG. 3 provides a schematic representation of a non-limiting example of this embodiment of the present invention.

The preceding examples and descriptions of the functionalized polyester biodegradable polymers of the present invention and their associated methods of manufacture are not intended to limit the present invention. They are merely representations of the myriad types of novel polymers that may be used to prepare implantable medical devices, in whole or in part, or coatings therefore.

As depicted in FIG. 3, once the biodegradable polymers of the present invention have been provided with functional groups attached to the polyester backbone, the functional groups may be further derivatized. In one embodiment of the present invention the functional group is further derivatized to convelently bond to a bioactive agent (drug). Many bioactive agents are so highly soluble in physiological tissues that they are too quickly released into the tissue and thus have either limited therapeutic life spans or reach toxic concentrations in situ. One advantage of the present invention is the ability of these biodegradable polymers to hold the bioactive agent in place as part of the polymer and release the bioactive agent as the biodegradable polymer naturally decomposes in vivo. The biodegradable polymers of the present invention can be fine tuned to biodegrade over a specified time period by increasing or decreasing the relative hydrophilicity of the polymer by modifying the functional groups attached to the polyester backbone.

Moreover, as can be seen in FIG. 3, in some embodiments of the present invention vinyl functionality is added to the polyester backbone. The presence of the carbon-carbon double bond provides a reactive group useful for many addition reactions as well as a site for intermolecular and intramolecular cross-linking. Such cross-linking can enhance mechanical properties of the polymer and aid in the controlled release of bioactive agents (the degree of cross-linking being inversely proportional to the release rate of many bioactive agents).

Furthermore, the vinyl group is extremely useful as a means for tuning the polymer's hydrophilicity. For example as hydroxyl groups are added the hydrophilicity increases as compared to the polyester backbone alone. It is also possible to add carboxylic acid groups to the polymers by first converting the oxo groups (in one embodiment, see FIG. 2) or acrylic groups (in another embodiment, see FIG. 3) to alcohols and then esterfying the alcohol. Having done this, the polymer becomes increasingly hydrophilic as well as providing cross-linking sites on the side chains. Additionally, the vinyl group can also serve as an initiation point for free radical polymerization.

EXAMPLES

The following non-limiting examples of the present invention provide further teachings that will allow those having ordinary skill in the art to practice the full scope of the present invention without undue experimentation. All reagents used are commercially available from standard sources such as, but not limited to, Sigma-Aldrich Chemicals, St. Louis, Mo., USA.

Example 1

Acrylic Functionalized Polyester Backbones

A) Monomer Synthesis

In a 500 mL tri-neck round-bottom flask add 10 mL of N,N-diiopropylamine and 300 mL of tetrahydrofuran (THF). Stir under nitrogen and cool in a dry ice isopropyl alcohol bath. To this reaction mixture add 24 mL of N-Butyl Lithium by syringe drop-wise and stir gently for 15 minutes. Next 30 mL of 20% (vol/vol) solution of δ-valerolactone in THF is added drop-wise over a 1 hour period, gently stir for 30 minutes and then 30 mL of a 20% (vol/vol) allyl bromide solution in THF is added drop-wise over 1 hour while gently stirring. Continue to gently stir the reaction mixture for 2 hours. Next 6 mL of a saturated ammonium chloride solution is added and the reaction mixture is allowed to warm to room temperature. Next volatiles are removed by rotary evaporation. The remaining solid is dissolved in ether, washed in saline and diluted with hexane followed by a second saline wash. The reaction product is then eluted through a chromatography column with a 15% ethyl acetate-in-hexane solution and then distilled. The final acrylic functionalized product (allyl valerolactone), is a viscous liquid.

B) Polymer Synthesis

Two grams of allyl valerolactone from step A is mixed with 8 grams of D,L-lactide and 0.025 grams of $Sn(Oct)_2$ in a suitable solvent and added to a 100 mL glass serum bottle containing a Teflon coated magnetic stir bar. The bottle is stoppered using a Teflon-coated silicone septum and then purged with nitrogen gas for approximately 20 minutes and then held for 72 hours at 140° C. in a silicon oil bath. After 72 hours the reaction product is recovered, dissolved in chloroform and precipitated in cold methanol; this is repeated three times. The final purified polymer is then dissolved in methanol, poured into PTFE trays and held over night at 50° C. under vacuum.

C) Hydroxyl Functionality

Two grams of the co-polymer from step B is dissolved in 20 mL of acetone to which 1.5 mL of a 50 weight percent aqueous solution of N-methylmorpholine-N-oxide (NMO) is added. This is followed by the addition of 76 mL of a 1 weight percent aqueous solution of osmium tertraoxide ($OsO_4$) to the reaction mixture which is then stirred and held for 24 hours at room temperature. The resulting reaction product is then washed in water and saline and then precipitated into hexane and dried over magnesium sulfate. Volatiles are removed using a rotary evaporator.

D) Phosphoryl Choline Functionality

One gram of the final polymer product from step C is dissolved in 25 mL of acetonitrile and placed in a bottle containing a stir bar; the bottle is sealed with a Teflon-coated silicon septum and cooled to −20° C. in a dry ice/isopropyl alcohol bath. Next 0.6 mL of trimethylamine (TMA) is added to the bottle via syringe and the reaction vessel and its contents are heated to 60° C. and maintained at same for 48 hours. The resulting product is filtered through silica gel and eluted with a 70/30 (volume/volume) mixture of water and ethanol. The product is distilled and then dried overnight at 50° C. under vacuum.

Example II

Hydroxyl Functionalized Polyester Backbones

A. Preparation of Oxo Functionalized Polyester

Cyclohxane 1,4 dione (CAS Reg Number 637-88-7) is reacted with m-chloroperbenzoic acid (m-CPBA CAS Reg Number 937-14-4) to yield the seven member heterocyclic dione oxepane-2,5-dione. This seven member heterocyclic dione is then reacted with a cyclic di-ester, 3,6 dimethyl-[1,4]dioxane 2,5 dione (D,L-Lactide) (CAS Reg Number 30846-39-0), in the presence of the ring opening catalyst $Sn(Oct)_2$ resulting in a ring-opening polymerization as depicted in FIG. 2.

B. Adding Hydroxyl Functionality

The polyester polymer is then modified to contain a hydroxyl group. This is done via known oxidation and/or hydroxyl adding processes. For example, it is well known that ketones can be reduced to secondary alcohols through nucelophilic addition (reduction) of the oxo group using hydride reagents such as, but not limited to $LiAlH_4$ and $NaBH_4$. It is understood that where more than one oxo is present and less than the total number of oxo groups are to be reduced that some oxo groups need to be protected. Persons having ordinary skill in the art of synthetic organic chemistry can design suitable protection techniques without undue experimentation.

The present invention is directed at engineering biocompatible, biodegradable polymers that provide optimized drug eluting medical devices and medical device coatings. Specifically, polymers made in accordance with teachings of the present invention provide biodegadable polymers for medical devices intended for use in hemodynamic environments. Recently, polymer technologies have been applied to implantable medical devices such as vascular stents, vascular stent grafts, urethral stents, bile duct stents, catheters, inflation catheters, injection catheters, guide wires, pace maker leads, ventricular assist devices, bone screws, joint repelcements and prosthetic heart valves. Devices such as these are generally subjected to flexion strain and stress during implantation, application or both. Providing flexible medical devices such as stents with stable biocompatible polymer coatings is especially difficult.

In one embodiment of the present invention vascular stents are provided with a controlled-release polymer using the compositions of the present invention. Vascular stents are chosen for exemplary purposes only. Those skilled in the art of material science and medical devices will realize that the polymer compositions of the present invention are useful in coating or fabricating a large range of medical devices. Therefore, the use of the vascular stent as an exemplary embodiment is not intended as a limitation.

Vascular stents present a particularly unique challenge for the medical device coating scientist. Vascular stents (hereinafter referred to as "stents") must be flexible, expandable, biocompatible and physically stable. Stents are used to relieve the symptoms associated with coronary artery disease caused by occlusion in one or more coronary artery. Occluded coronary arteries result in diminished blood flow to heart muscles causing ischemia-induced angina and, in severe cases, myocardial infarcts and death. Stents are generally deployed using catheters having the stent attached to an inflatable balloon at the catheter's distal end. The catheter is inserted into an artery and guided to the deployment site. In many cases the catheter is inserted into the femoral artery of the leg or carotid artery and the stent is deployed deep within the coronary vasculature at an occluded site ("treatment site").

Vulnerable plaque stabilization is another application for polymeric drug-eluting vascular stents and stent coatings. Vulnerable plaque is composed of a thin fibrous cap covering a liquid-like core composed of an atheromatous gruel. The exact composition of mature atherosclerotic plaques varies considerably and the factors that affect an atherosclerotic plaque's make-up are poorly understood. However, the fibrous cap associated with many atherosclerotic plaques is formed from a connective tissue matrix of smooth muscle cells, types I and III collagen and a single layer of endothelial cells. The atheromatous gruel is composed of blood-borne lipoproteins trapped in the sub-endothelial extracellular space and the breakdown of tissue macrophages filled with low density lipids (LDL) scavenged from the circulating blood. (G. Pasterkamp and E. Falk. 2000. Atherosclerotic Plaque Rupture: An Overview. J. Clin. Basic Cardiol. 3:81-86). The ratio of fibrous cap material to atheromatous gruel determines plaque stability and type. When atherosclerotic plaque is prone to rupture due to instability it is referred to a "vulnerable" plaque. Upon rupture the atheromatous gruel is released into the blood stream and induces a massive thrombogenic response leading to sudden coronary death. Recently, it has been postulated that vulnerable plaque can be stabilized by stenting the plaque. Moreover, vascular stents having a drug-releasing coating composed of matrix metalloproteinase inhibitor dispersed in, or coated with (or both) a polymer may further stabilize the plaque and eventually lead to complete healing.

Treatment of aneurysms is yet another application for drug-eluting stents. An aneurysm is a bulging or ballooning of a blood vessel usually caused by atherosclerosis. Aneurysms occur most often in the abdominal portion of the aorta. At least 15,000 Americans die each year from ruptured abdominal aneurysms. Back and abdominal pain, both symptoms of an abdominal aortic aneurysm, often do not appear until the aneurysm is about to rupture, a condition that is usually fatal. Stent grafting has recently emerged as an alternative to the standard invasive surgery. A vascular graft containing a stent (stent graft) is placed within the artery at the site of the aneurysm and acts as a barrier between the blood and the weakened wall of the artery, thereby decreasing the pressure on artery. The less invasive approach of stent-grafting aneurysms decreases the morbidity seen with conventional aneurysm repair. Additionally, patients whose multiple medical comorbidities make them excessively high risk for conventional aneurysm repair are candidates for stent-grafting. Stent grafting has also emerged as a new treatment for a related condition, acute blunt aortic injury, where trauma causes damage to the artery.

Once positioned at the treatment site the stent or graft is deployed. Generally, stents are deployed using balloon catheters. The balloon expands the stent, gently compressing it against the arterial lumen clearing the vascular occlusion or stabilizing the aneurysm. The catheter is then removed and the stent remains in place either permanently, or for a predetermined time period if the entire stent comprises the biodegradable polymers of the present invention. Most patients return to a normal life following a suitable recovery period and have no reoccurrence of coronary artery disease associated with the stented occlusion. However, in some cases the arterial wall's intima is damaged either by the disease process itself or as the result of stent deployment. This injury initiates a complex biological response culminating in vascular smooth muscle cell hyperproliferation and occlusion, or restenosis at the stent site.

Recently significant efforts have been devoted to treating and preventing restenosis. Several techniques including brachytherapy, excimer laser, and pharmacological techniques have been developed. The least invasive and most promising treatment modality is the pharmacological approach. A preferred pharmacological approach involves the site-specific delivery of cytostatic or cytotoxic drugs directly to the stent deployment area. Site-specific delivery is preferred over systemic delivery for several reasons. First, many cytostatic and cytotoxic drugs are highly toxic and cannot be administered systemically at concentrations needed to prevent restenosis. Moreover, the systemic administration of drugs can have unintended side effects at body locations remote from the treatment site. Additionally, many drugs are either not sufficiently soluble, or too quickly cleared from the blood stream to effectively prevent restenosis. Therefore, administration of anti-restenotic compounds directly to the treatment area is preferred.

Several techniques and corresponding devices have been developed to deploy anti-restenotic compounds including weeping balloon and injection catheters. Weeping balloon catheters are used to slowly apply an anti-restenotic composition under pressure through fine pores in an inflatable segment at or near the catheter's distal end. The inflatable segment can be the same used to deploy the stent or a separate segment. Injection catheters administer the anti-restenotic composition by either emitting a pressurized fluid jet, or by directly piercing the artery wall with one or more needle-like appendage. Recently, needle catheters have been developed to inject drugs into an artery's adventitia. However, administration of anti-restenotic compositions using weeping and injection catheters to prevent restenosis remains experimental and largely unsuccessful. Direct anti-restenotic composition administration has several disadvantages. When anti-restenotic compositions are administered directly to the arterial lumen using a weeping catheter, the blood flow quickly flushes the anti-restenotic composition down stream and away from the treatment site. Anti-restenotic compositions injected into the lumen wall or adventitia may rapidly diffuse into the surrounding tissue. Consequently, the anti-restenotic composition may not be present at the treatment site in sufficient concentrations to prevent restenosis. As a result of these and other disadvantages associated with catheter-based local drug delivery, investigators continue to seek improved methods for the localized delivery of anti-restenotic compositions.

Figure 4:
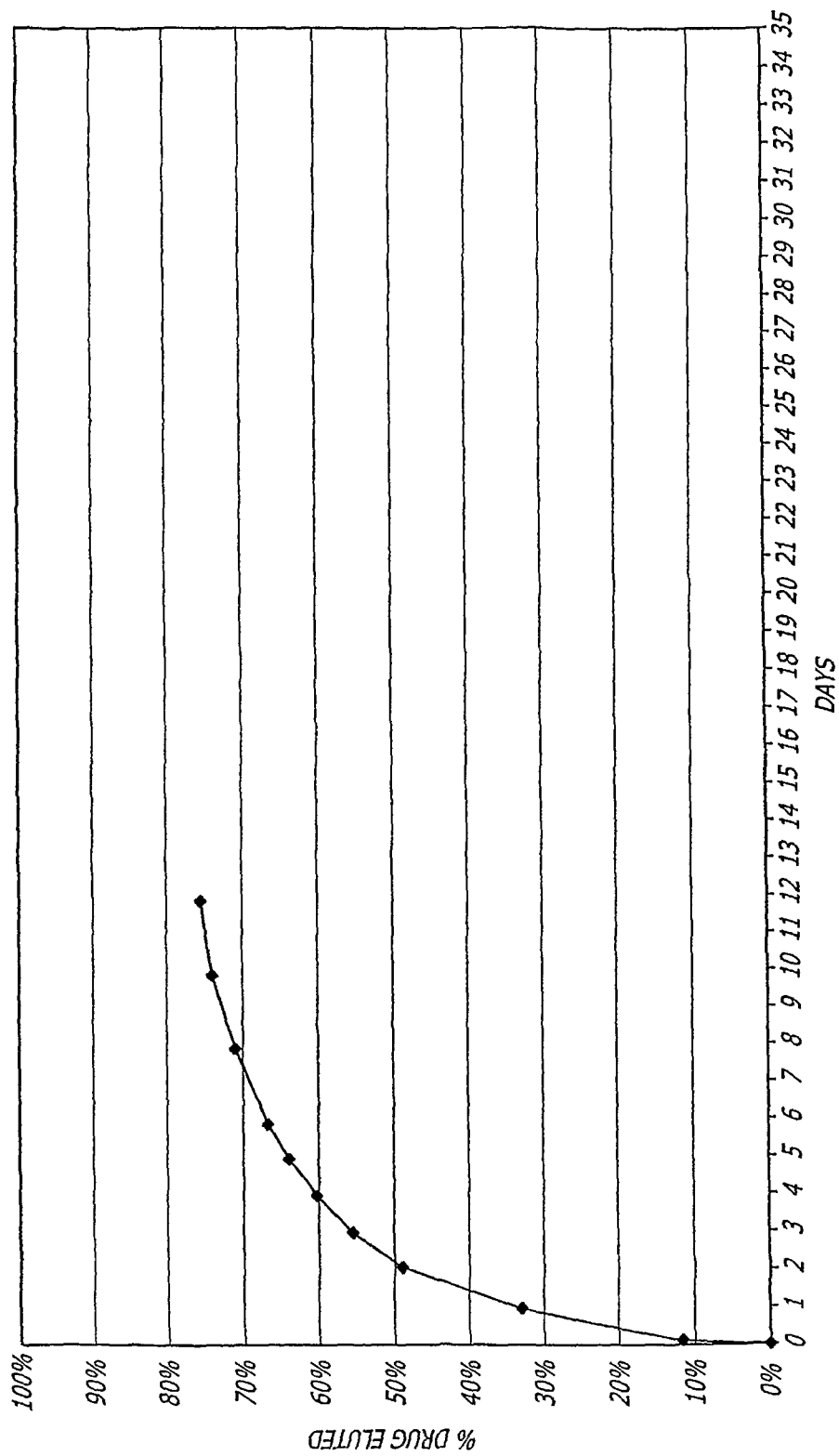
FIG. 4 graphically depicts idealized first-order kinetics associated with drug release from a polymer coating.
Figure 5:
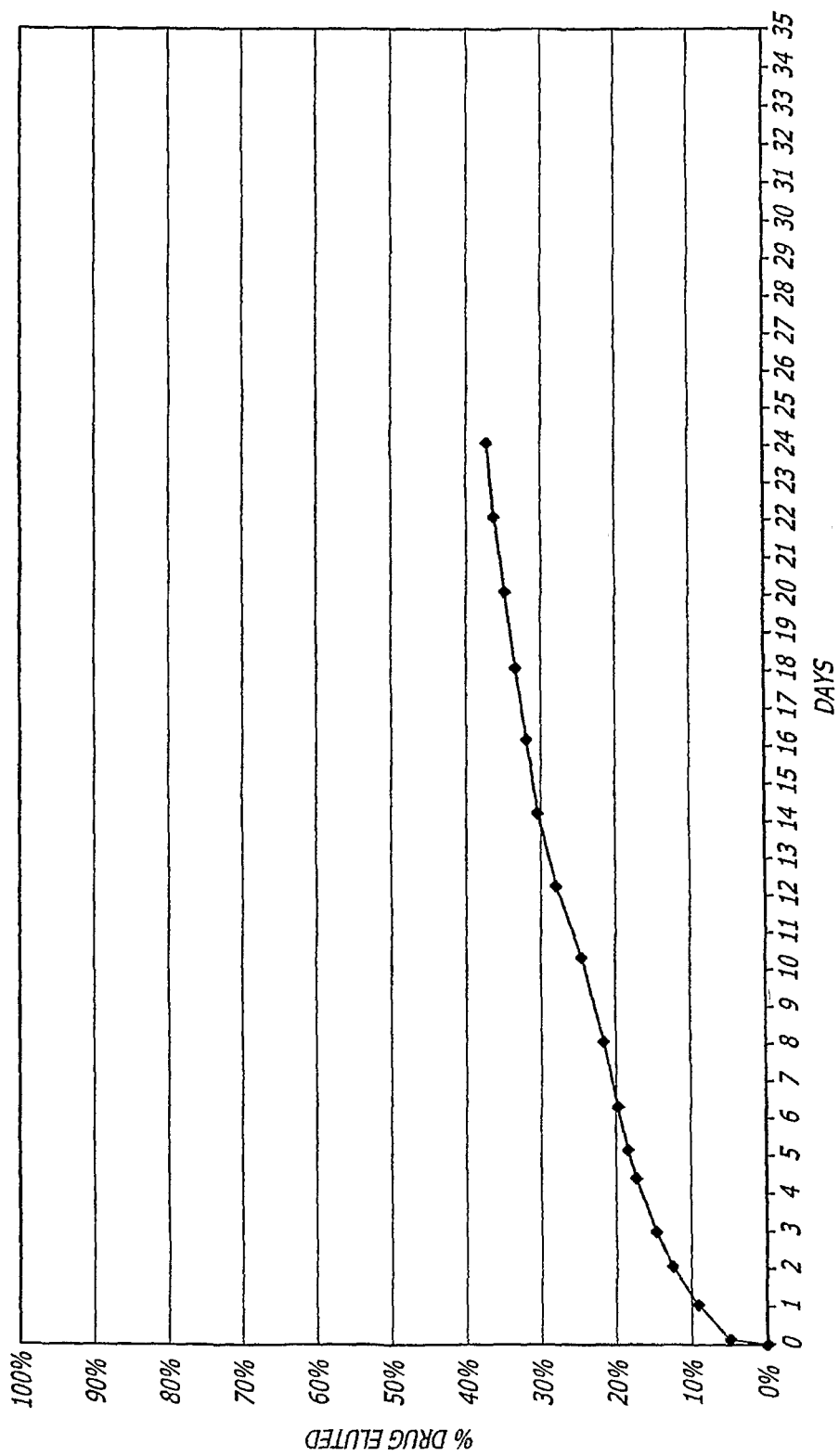
FIG. 5 graphically depicts idealized zero-order kinetics associated with drug release from a polymer coating.

The most successful method for localized anti-restenotic composition delivery developed to date is the drug-eluting stent (DES). Many DES embodiments have been developed and tested. However, significant advances are still necessary in order to provide safe and highly effective drug delivery stents. One of the major challenges associated with stent-based anti-restenotic composition delivery is controlling the drug delivery rate. Generally speaking, drug delivery rates have two primary kinetic profiles. Drugs that reach the blood stream or tissue immediately after administration follow first-order kinetics. FIG. 4 graphically depicts idealized first-order kinetics. First-order drug release kinetics provide an immediate surge in blood or local tissue drug levels (peak levels) followed by a gradual decline (trough levels). In most cases therapeutic levels are only maintained for a few hours. Drugs released slowly over a sustained time where blood or tissue concentrations remains steady follow zero-order kinetics. FIG. 5 graphically depicts idealized zero-order kinetics. Depending on the method of drug delivery and tissue/blood clearance rates, zero-order kinetics result in sustained therapeutic levels for prolonged periods. Drug-release profiles can be modified to meet specific applications. Generally, most controlled release compositions are designed to provide near zero-order kinetics. However, there may be applications where an initial burst, or loading dose, of drug is desired (first-order kinetics) followed by a more gradual sustained drug release (near zero-order kinetics).

The present invention is directed at optimized drug releasing medical device coatings and medical devices themselves comprised entirely, or nearly entirely form biodegradable polymers of the present invention that are suitable for use in hemodynamic environments. The coatings and devices of the present invention may also have at least one bioactive compound or drug dispersed therein.

In addition to the aforementioned structural and drug-releasing profile considerations, polymers used as stent coatings must also be biocompatible. Biocompatibility encompasses numerous factors that have been briefly defined in the preceding "Definition of Terms" section. The need for a polymer to be biocompatible significantly limits the number of available options for the material scientist. Moreover, these options are further limited when the polymer coating is used on a device that is continuously exposed to hemodynamic forces. For example, stent coatings must remain non-thrombogenic, non-inflammatory and structurally stable for prolonged time periods.

Therefore, there are four specific attributes that the stent coating polymers made in accordance with the teachings of the present invention should possess. The polymer compositions of the present invention should be biocompatible, degrade at a predetermined rate, be elastic/ductile and possess a predetermined drug release profile. Other requirements include processing compatibility such as inert to sterilization methods including, but not limited to, ethylene oxide sterilization Release rate is not entirely a function of drug-polymer compatibility. Coating configurations, polymer swellability, and coating thickness also play roles. Moreover, the present invention provides yet another means for controlling drug elution rates. By tuning the biodegradable polymers of the present invention to degrade at a specific rate, drug elution can be precisely controlled and ceases entirely with the complete degradation of the polymer.

When the medical device of the present invention is used in the vasculature, the coating dimensions are generally measured in micrometers (μm). Coatings consistent with the teaching of the present invention may be a thin as 1 μm or a thick as 1000 μm. There are at least two distinct coating configurations within the scope of the present invention. In one embodiment of the present invention the drug-containing coating is applied directly to the device surface or onto a polymer primer. Depending on the solubility rate and profile desired, the drug is either entirely soluble within the polymer matrix, or evenly dispersed throughout. The drug concentration present in the polymer matrix ranges from 0.1% by weight to 80% by weight. In either event, it is most desirable to have as homogenous of a coating composition as possible. This particular configuration is commonly referred to as a drug-polymer matrix.

Finally, returning to coating thickness, while thickness is generally a minor factor in determining overall drug-release rates and profile, it is nevertheless an additional factor that can be used to tune the coatings. Basically, if all other physical and chemical factors remain unchanged, the rate at which a given drug diffuses through a given coating is directly proportional to the coating thickness. That is, increasing the coating thickness increases the elution rate and visa versa.

We now turn to another factor that contributes to the compatiblized, biodegradable controlled release coatings of the present invention. As mentioned earlier, coating intended for medical devices deployed in a hemodynamic environment must possess excellent adhesive properties. That is, the coating must be stably linked to the medical device surface. Many different materials can be used to fabricate the implantable medical devices including stainless steel, nitinol, aluminum, chromium, titanium, ceramics, and a wide range of synthetic polymeric and natural materials including collagen, fibrin and plant fibers. All of these materials, and others, may be used with the controlled release coatings made in accordance with the teachings of the present invention. Furthermore, the biodegradable polymers of the present invention can be used to fabricate an entire medical device such that the bioactive agent is dispersed throughout the polymer and released as the device degrades. This feature of the present invention is particularly useful when the device is implanted into remote regions of the body where subsequent removal, should it be required, is either not possible or involves complex, high risk surgical procedures.

Figure 6:
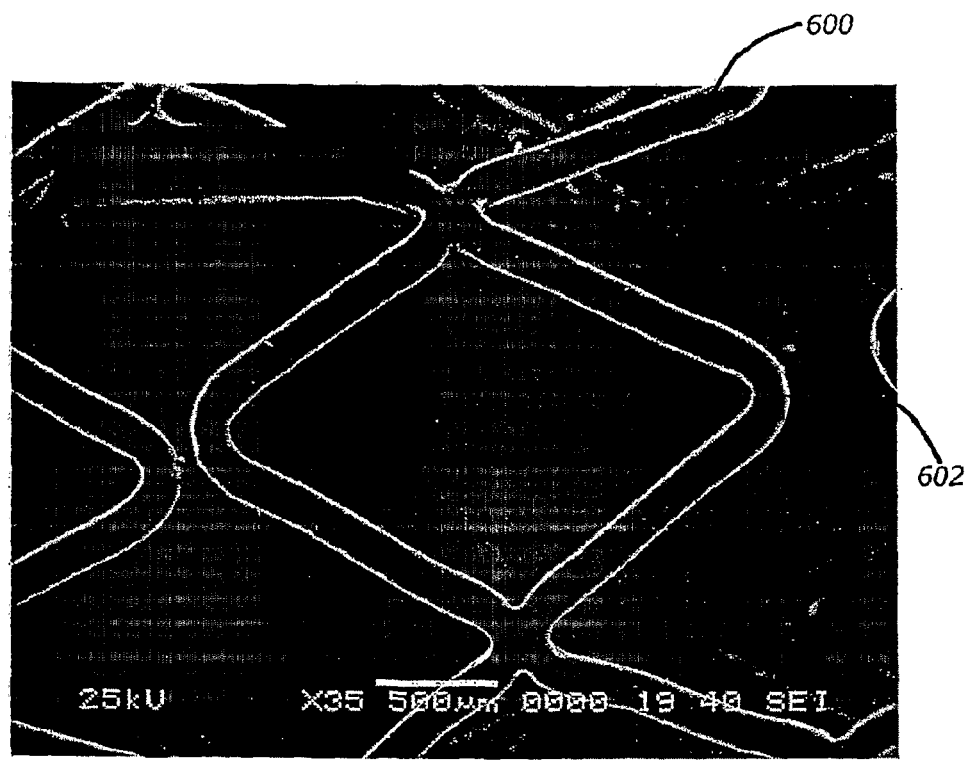
FIG. 6 depicts a vascular stent used to deliver the anti-restenotic compounds of the present invention.

One embodiment of the present invention is depicted in FIG. 6. In FIG. 6 a vascular stent 600 having the structure 602 is made from a material selected from the non-limiting group of materials including stainless steel, nitinol, aluminum, chromium, titanium, ceramics, and a wide range of synthetic polymeric and natural materials including collagen, fibrin and plant fibers. The structure 602 is provided with a coating composition made in accordance with the teachings of the present invention.

Figure 7:
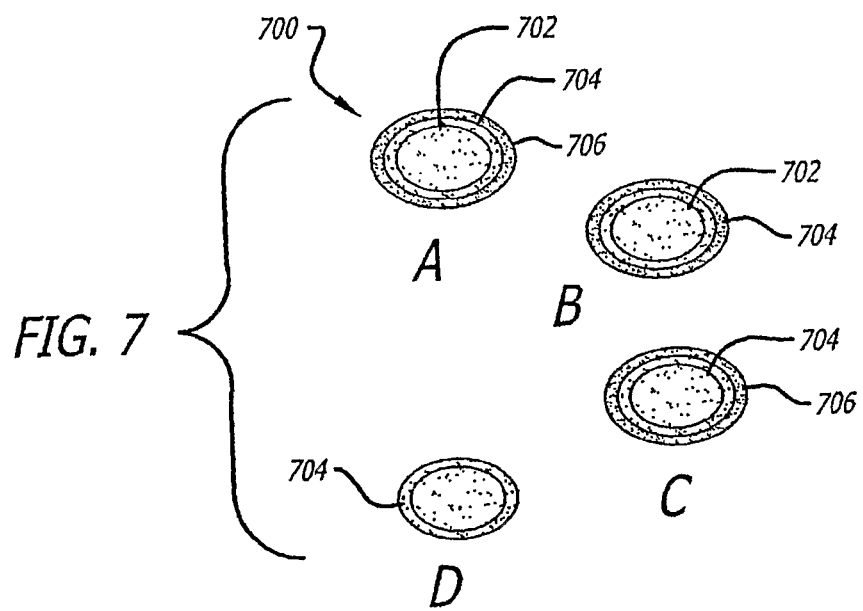
FIG. 7 depicts cross sections of medical devices (stents) having various drug-eluting coatings made in accordance with the teachings of the present invention.
Figure 8:
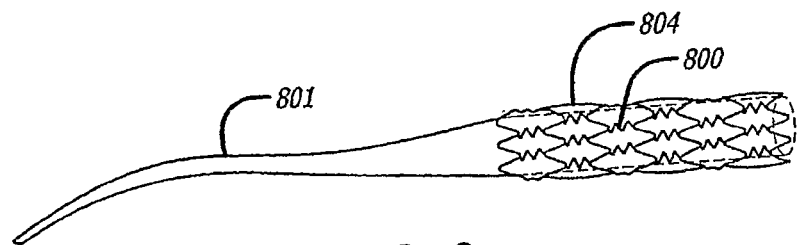
FIG. 8 depicts a balloon catheter assembly used for angioplasty and the site-specific delivery of stents to anatomical lumens at risk for restenosis.

FIGS. 7a-d are cross-sections of stent 700 showing various coating configurations. In FIG. 7a stent 700 has a first polymer coating 702 comprising an optional medical grade primer, such as but not limited to parylene; a second controlled release coating 704; and a third barrier, or cap, coat 706. In FIG. 7b stent 700 has a first polymer coating 702 comprising an optional medical grade primer, such as but not limited to parylene and a second controlled release coating 704. In FIG. 7c stent 700 has a first controlled release coating 704 and a second barrier, or cap, coat 706. In FIG. 7d stent 700 has only a controlled release coating 704. FIG. 8 depicts a vascular stent 800 having a coating 804 made in accordance with the teachings of the present invention mounted on a balloon catheter 801.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The controlled-release coatings of the present invention can be applied to medical device surfaces, either primed or bare, in any manner known to those skilled in the art. Application methods compatible with the present invention include, but are not limited to, spraying, dipping, brushing, vacuum-deposition, and others. Moreover, the controlled-release coatings of the present invention may be used with a cap coat. A cap coat as used herein refers to the outermost coating layer applied over another coating. A drug-releasing copolymer coating is applied over the primer coat. A polymer cap coat is applied over the drug-releasing copolymer coating. The cap coat may optionally serve as a diffusion barrier to further control the drug release, or provide a separate drug. The cap coat may be merely a biocompatible polymer applied to the surface of the sent to protect the stent and have no effect on elution rates. One aspect of the present invention is to provide a biodegradable cap coat that protects the device and bioactive agent from the environment until implanted. After implantation is complete, the biodegradable cap coat degrades at a predetermined rate (made possible by the addition and modification of functional groups to the polymer backbone as made in accordance with the teachings of the present invention) exposing the medical device surface and bioactive agent to the physiological environment.

As discussed above, medical devices can be fabricated from the polymeric compounds of the present invention using a variety of methods. For exemplary, non-limiting, purposes a biodegradable vascular stent will be described. In the one embodiment the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube.

In the braided stent embodiment monofilaments are fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a temperature between about the polymer-glass transition temperature and the melting temperature of the polymer blend for a time period between about five minutes and about 18 hours in air, an inert atmosphere or under vacuum. The stent is then allowed to cool and is then cut.

The extruded tubular stent of the present invention is formed by first melting the pelletized polymer in the barrel of an injection molding machine and then injected into a mold under pressure where it is allowed to cool and solidify. The stent is then removed from the mold. The stent made in accordance with the teachings of the present invention may, or may not, be molded with fenestrations in the stent tube. In a preferred embodiment of the fenestrated stent the tube blank is injection molded or extruded, preferably injection molded, without fenestrations. After cooling, fenestrations are cut into the tube using die-cutting, machining or laser cutting, preferably laser cutting. The resulting fenestrations, or windows, may assume any shape which does not adversely affect the compression and self-expansion characteristics of the final stent.

The stent is then disposed on an annealing mandrel having an outer diameter of equal to or less than the inner diameter of the stent and annealed at a temperature between about the polymer-glass transition temperature and the melting temperature of the polymer blend for a time period between about five minutes and 18 hours in air, an inert atmosphere or under vacuum. The stent is allowed to cool and then cut as required.

Stents made in accordance with the teachings of the present invention have mechanical properties and strength that generally increase proportionally with the molecular weight of the polymers used. The optimum molecular weight range is selected to accommodate processing effects and yield a stent with desired mechanical properties and in vivo degradation rate.

Two physical qualities of the polymer or polymer blend used to fabricate the stent play important roles in defining the overall mechanical qualities of the stent: tensile strength and tensile modulus. Tensile strength is defined as the force per unit area at the breaking point. It is the amount of force, usually expressed in pounds per square inch (psi), that a substrate can withstand before it breaks, or fractures. The tensile modulus, expressed in psi, is the force required to achieve one unit of strain which is an expression of a substrate's stiffness, or resistance to stretching, and relates directly to a stent's self-expansion properties.

Tensile strength and tensile modulus are physical properties that define a self-expanding stent's performance characteristics; these properties include compression resistance and self-expansion, or radial expansion, force. Compression resistance relates to the stent's ability to withstand the surrounding tissue's circumferential pressure. A stent with poor compression resistance will not be capable of maintaining patency. Self expansion force determines the stent's capacity to restore patency to a constricted lumen once inserted. The combination of self-expansion with resistance to compression is competing qualities and must be carefully considered when a stent is designed.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable medical device having a coating comprising: a biocompatible, biodegradable polymer of Formula I:

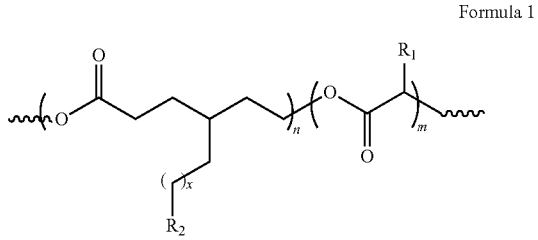

Formula 1 wherein n and m are separately integers from 1 to 100, X is an integer from 0 to 20, $R_1$ is hydrogen or a $C_1$-$C_{10}$ straight chain or branched alkyl or a $C_1$-$C_{10}$ straight chain or branched alkenyl and $R_2$ is a functional group selected from the group consisting of oxo, hydroxyl, carboxylic acid, amino, vinyl, poly(ethylene glycol) and phosphoryl choline.

2. The implantable medical device according to claim 1 wherein said implantable medical device selected from the group consisting of a vascular stent, a stent graft, a heart valve, a catheter, a pacemaker and a bone screw.

3. The implantable medical device according to claim 1 wherein $R_1$ is methyl, X equals 1 and $R_2$ is phosphoryl choline.

4. The implantable medical device according to claim 1 wherein said coating further comprises a bioactive agent selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-sense nucleotides and transforming nucleic acids.

5. The implantable medical device according to claim 4 wherein said coating comprises an anti-proliferative agent.

6. The implantable medical device according to claim 5 wherein said anti-proliferative is a chemotherapeutic agent.

7. The implantable medical device according to claim 6 wherein said chemotherapeutic agent is zotarolimus.

8. The implantable medical device according to claim 1 wherein said implantable medical device is a vascular stent.

9. A vascular stent comprising the coating of claim 1 wherein said coating further comprises zotarolimus in an amount that inhibits or treats restenosis.

10. An implantable medical device having a coating comprising: a biocompatible, biodegradable polymer of Formula I:

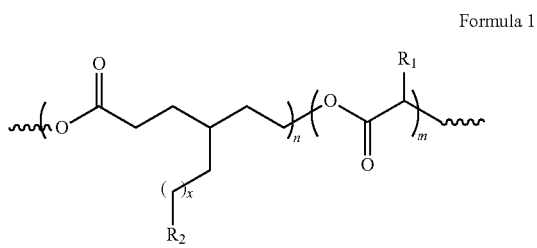

Formula 1 wherein n and in are separately integers from 1 to 100, X is an integer from 0 to 20, $R_1$ is hydrogen or a $C_1$-$C_{10}$ straight chain or branched alkyl or a $C_1$-$C_{10}$ straight chain or branched alkenyl and $R_2$ is a functional group selected from the group consisting of oxo, hydroxyl, carboxylic acid, amino, vinyl, and poly(ethylene glycol).

11. The implantable medical device according to claim 10 wherein said coating further comprises a bioactive agent selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-sense nucleotides and transforming nucleic acids.

12. The implantable medical device according to claim 11 wherein said coating comprises an anti-proliferative which is a chemotherapeutic agent.

13. The implantable medical device according to claim 12 wherein said chemotherapeutic agent is zotarolimus.

* * * * *